US011599186B2

(12) United States Patent
Lympouridis et al.

(10) Patent No.: US 11,599,186 B2

(45) Date of Patent: Mar. 7, 2023

(54) RESPIRATION MONITORING DEVICES, SYSTEMS AND PROCESSES FOR MAKING THE SAME

(71) Applicant: AppliedVR., Inc., Los Angeles, CA (US)

(72) Inventors: Vangelis Lympouridis, Los Angeles, CA (US); Derek Nielsen, Los Angeles, CA (US); Josh Sackman, Los Angeles, CA (US)

(73) Assignee: AppliedVR., Inc., Los Angeles, CA (US)

( * ) Notice: Subject to any disclaimer, the term of this patent is extended or adjusted under 35 U.S.C. 154(b) by 850 days.

(21) Appl. No.: 16/534,961

(22) Filed: Aug. 7, 2019

(65) Prior Publication Data

US 2020/0397342 A1 Dec. 24, 2020

Related U.S. Application Data

(60) Provisional application No. 62/865,910, filed on Jun. 24, 2019.

(51) Int. Cl.

*A61B 5/00* (2006.01)
*G06F 3/01* (2006.01)
(Continued)

(52) U.S. Cl.

CPC ............ *G06F 3/011* (2013.01); *A61B 5/0022* (2013.01); *A61B 5/0816* (2013.01); *A61B 5/097* (2013.01); *A61B 5/486* (2013.01); *A61B 5/6803* (2013.01); *A61B 5/6814* (2013.01); *G06F 3/16* (2013.01); *G10L 21/0316* (2013.01); *G10L 25/18* (2013.01); *G10L 25/51* (2013.01); *A61B 5/0205* (2013.01); *A61B 5/681* (2013.01); *G02B 27/0176* (2013.01); *G06F 3/165* (2013.01); *G06F 2203/011* (2013.01)

(58) Field of Classification Search

CPC .... G06F 3/011; G06F 3/165; G06F 2203/011; G06F 3/16; A61B 5/0022; A61B 5/0205; A61B 5/0816; A61B 5/097; A61B 5/486; A61B 5/681; A61B 5/6814; G10L 21/0316; G10L 25/18; G10L 25/51; G02B 27/0176

See application file for complete search history.

(56) References Cited

U.S. PATENT DOCUMENTS

2011/0004327 A1* 1/2011 Bonnat .................. G06F 3/011 700/83

2017/0168303 A1* 6/2017 Petrov ............... G02B 27/0176

(Continued)

*Primary Examiner* — Adam J Snyder

(74) *Attorney, Agent, or Firm* — Adam P. Daniels, Esq.; Polsinelli LLP

(57) ABSTRACT

A device for directing respired air includes a frame having a top portion, a bottom portion opposite the top portion, and at least one shoulder disposed between the top portion and the bottom portion to receive a portion of a headset. The device further includes an attachment mechanism coupled to the frame for releasably securing the frame to the headset. In addition, the device also includes a wall surface downwardly depending from the bottom portion of the frame to form a curved baffle. The curved baffle directs air corresponding to respiration toward the bottom portion of the frame, and thus toward an input interface of the headset when the frame is releasably secured to the headset.

20 Claims, 9 Drawing Sheets

100
102
104
110
112
206
204
114
$\ell_1$
$\ell_2$
202
d

(51) Int. Cl.

| | |
|---|---|
| ***G06F 3/16*** | (2006.01) |
| ***G10L 21/0316*** | (2013.01) |
| ***G10L 25/18*** | (2013.01) |
| ***G10L 25/51*** | (2013.01) |
| ***A61B 5/08*** | (2006.01) |
| ***A61B 5/097*** | (2006.01) |
| *A61B 5/0205* | (2006.01) |
| *G02B 27/01* | (2006.01) |

(56) References Cited

U.S. PATENT DOCUMENTS

| | | | | |
|---|---|---|---|---|
| 2017/0266676 | A1* | 9/2017 | Fateh | A63F 13/212 |
| 2018/0173308 | A1* | 6/2018 | Smith | G06F 3/015 |
| 2018/0256440 | A1 | 9/2018 | Francois et al. | |
| 2018/0272189 | A1* | 9/2018 | Lee | G06F 3/011 |
| 2018/0348863 | A1* | 12/2018 | Aimone | G06F 3/015 |
| 2019/0019508 | A1* | 1/2019 | Rochford | G06F 3/013 |
| 2020/0383581 | A1 | 12/2020 | Su et al. | |
| 2021/0373602 | A1* | 12/2021 | Min | G06F 3/017 |

* cited by examiner

RESPIRATION MONITORING DEVICES, SYSTEMS AND PROCESSES FOR MAKING THE SAME

CROSS REFERENCE TO RELATED APPLICATIONS

This application claims the benefit of U.S. Provisional Patent Application Ser. No. 62/865,910, entitled "RESPIRATION MONITORING DEVICES, SYSTEMS AND PROCESSES FOR A WEARABLE HEADSET," filed Jun. 24, 2019, the entirety of which is incorporated herein by reference.

TECHNICAL FIELD

The present disclosure generally relates to portable devices, and more specifically to devices that facilitate monitoring user respiration and providing biofeedback using a headset.

BACKGROUND

Portable devices such as mobile phones, tablets, smart watches, digital headsets (e.g., Virtual Reality (VR) headsets), and the like have become a mainstay in daily life due to advances in consumer technology, including decreased costs, reduced form factors, increased processing power, improved displays and control interfaces, and so on. The readily accessible nature of such portable devices, in turn, provides new opportunities for businesses to interface and interact with consumers. For example, a number of portable devices have sensors (e.g., gyroscopes, accelerometers, cameras, photo detectors, microphones, etc.) that measure physiological and/or biological activity of a user, and interfaces (e.g. visual displays, speakers, haptic feedback hardware, etc.) that provide meaningful data to the user in the form of biofeedback data. Indeed, a variety of industries leverage biofeedback data to improve user experiences and increase user engagement. However, the true value derived from the biofeedback data for a given user is tied to an underlying accuracy of the measured physiological and/or biological activity.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

An element or functionally similar component is indicated with the same reference number.

DESCRIPTION OF EXAMPLE EMBODIMENTS

Overview

Figure 1:
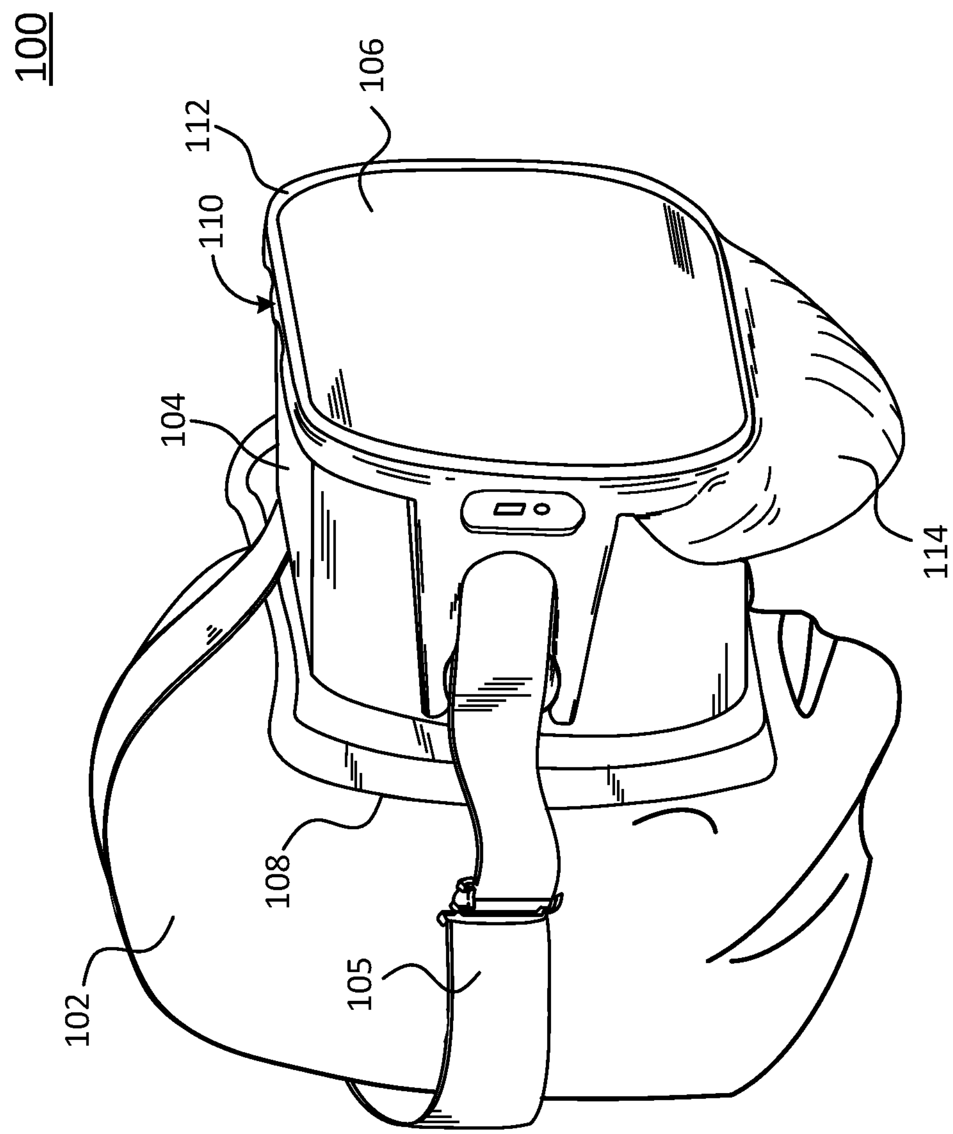
FIG. 1 illustrates a front perspective view of a respiration monitoring system, which includes a respiration guide device coupled to a wearable headset according to one exemplary embodiment of this disclosure.

The present disclosure is directed to portable devices that monitor physiological and/or biological activity of a user and provide biofeedback data representing the same. For example, the present disclosure describes respiration devices that facilitate monitoring respiration using a portable device such as a wearable headset. In one embodiment, the device facilitates monitoring the respiration of a user by directing or guiding air corresponding to respiration toward an input interface on the headset. For example, the device includes a frame having a top portion, a bottom portion opposite the top portion, and at least one shoulder disposed between the top portion and the bottom portion. The shoulder is operable or configured to receive a portion of a headset (e.g., a virtual reality (VR) headset). The device also includes an attachment mechanism coupled to the frame to releasably secure the frame to the headset. In addition, the device further includes a wall surface that downwardly depends from a bottom portion of the frame to form a curved baffle. The curved baffle operably directs the air toward the bottom portion of the frame. The headset can include an input interface (e.g., a microphone, anemometers, vibration films, thermal sensors, speaker, and the like) that detects and measures metrics corresponding to the respired air. Notably, when the frame is attached or coupled to the headset, the input interface is typically located proximate to the bottom portion of the frame (e.g., depending on the manufacturer of the headset). In this fashion, the curved baffle directs respired air toward the bottom portion of the frame, and thus, directs the respired air toward the input interface of the headset (e.g., when the frame is attached to the headset).

DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

As used herein, the term "portable device(s)" refers to electronic devices able to be easily transported by a user (e.g., a human). Examples of portable devices include, but are not limited to mobile phones, tablets, smart watches, Virtual Reality (VR) headsets, and the like. As used herein, the term "headset" or "wearable headset" refers to a type of portable device that can be worn on a user's head. It is appreciated that some portable devices (e.g., mobile phones) can be mounted in harnesses worn on a user's head. Thus, in this context, mobile phones may be considered a "headset" or "wearable headset."

As used herein, the term "sound" refers to vibrations that travel through air (or another medium), and includes vibrations corresponding to audible frequencies (e.g., intelligible by a person) as well as non-audible frequencies (e.g., detectable by a computer or electronic device).

As used herein, the terms "front," "back," "rear," "upper," "lower," "right," "left," "top," "bottom," "interior," and "exterior," in this description identify relative spatial relationships between various elements as they are oriented in the figures. It is appreciated that these terms are not meant to limit the element which they describe, as the various elements may be oriented differently in different views and in different applications.

As used herein, the term "coupled" refers to joining two members or components directly or indirectly to one another. Such joining may be stationary in nature or movable in nature and/or such joining may allow for an exchange of electricity, electrical signals, or other types of signals or communication between two members. Such joining may be achieved with the two members only or with the two members and additional intermediate members. Further, such joining may be achieved by integrally forming the two members as a single unitary body or by a physical or electrical connection between the two members (including shared connections with any intermediate members). In this fashion, the joining between two members may be removable, releasable, and/or permanent in nature.

As mentioned above, portable consumer devices are a mainstay in daily life, and provide new opportunities for interfacing and interacting with consumers. Indeed, many portable devices include sensors and interfaces that monitor physiological and/or biological activity, and provide meaningful data in the form of biofeedback. Biofeedback can improve user experiences and increase user engagement, and has increasingly become prevalent in a variety of industries, including entertainment, gaming, and health and wellness industries (e.g., which can include medical applications). Biofeedback can be passively presented to a user (e.g., displaying user's heart rate) and/or it can be dynamically incorporated into content presented to a user, where the content is adjusted or modified based on physiological/biological activity (e.g., playing a certain song on a playlist based on physical activity). In this fashion, biofeedback can improve a connection between a user and the user's internal biological processes and even create a connection between the user and presented content. Regardless of use-cases and presentment to the user, the true value of biofeedback is tied to the underlying accuracy of measured activity. Accordingly, this disclosure describes devices, systems, and processes that improve monitoring and measuring biofeedback corresponding to respiration of a user.

Referring now to the figures, FIG. 1 illustrates a front perspective view of one exemplary embodiment of a respiration monitoring system 100. As shown, respiration monitoring system 100 includes a headset 104 worn by a user 102, and a respiration guide device 110. Here, respiration guide device 110 is attached or coupled to headset 104.

Headset 104 is a digital device, and can include a virtual reality (VR) device, an augmented reality (AR) device, an enhanced reality (ER) device, and so on. While headset 104 is shown as a particular type of VR device, it is appreciated that headset 104 is representative or any type of wearable headset. For example, in some embodiments, headset 104 may only include a harness for mounting a mobile device or mobile phone of user 102.

Headset 104 includes a front portion 108, a rear portion 106 (e.g., opposite the front portion), and a strap 105 that secures headset 104 to a user's head—e.g., strap 105 shown as a harness worn around the user's head. Front portion 108 interfaces with the head of user 102, and more particularly, a face of user 102. As is appreciated by those skilled in the art, headset 104 includes hardware and software (not shown) for presenting digital content to user 102. For example, the hardware and software can include internal processors, memory, and display interfaces for presenting and creating a VR environment for user 102.

Respiration guide device 110 includes a frame 112 that couples to rear portion 106 of headset 104. As shown, frame 112 surrounds rear portion 106. While frame 112 is shown as surrounding a perimeter of rear portion 106, in some embodiments, frame 112 may only surround a portion of the perimeter of rear portion 106. Respiration guide device 110 also includes wall surface that downwardly depends or extends from frame 112 to form a curved baffle 114. Curved baffle 114 operably directs and/or guides air corresponding to respiration (e.g., a user's respiration such as an inhalation or exhalation). Notably, the air corresponding to the respiration can include sounds. Here, curved baffle 114 directs the air toward a bottom portion of frame 112, and thus, toward an input component (not shown) of headset 104. In general, curved baffle 114 forms a curved surface similar to a parabolic reflector, which collects and directs the air toward a focus. Here, the focus of curved baffle 114 corresponds to a position or location of the input component of headset 104 when headset 104 is attached to frame 112. Notably, it is appreciated that while curved baffle 114 is illustrated and described as having specific curvatures, this "curvature" may be also achieved by a number of flat sections disposed at relative angles, where the collective angles of the flat sections form the "curvature" of curved baffle 114.

As illustrated and discussed herein, curved baffle 114 is generally symmetrical about a centerline of frame 112 (not shown), however it is appreciated that such symmetry may be modified depending on the position of the input component of headset 104 relative to source of the respired air and/or the sound (e.g., a user's mouth). Further, it is also appreciated that the curvature of curved baffle 114 may include multiple curvatures that can be described as spherical, elliptical, and/or parabolic depending on the point of view or cross-section. For example, the curvature of baffle 114 may be described as parabolic when viewed at a horizontal or lateral cross-section, such as the cross-sectional view of FIG. 5C (viewed from cut lines 5-5 in FIG. 3), or spherical when viewed at a vertical or longitudinal cross-section, such as the cross-sectional view of FIG. 7 (viewed from cut lines 7-7 in FIG. 6).

Figure 2:
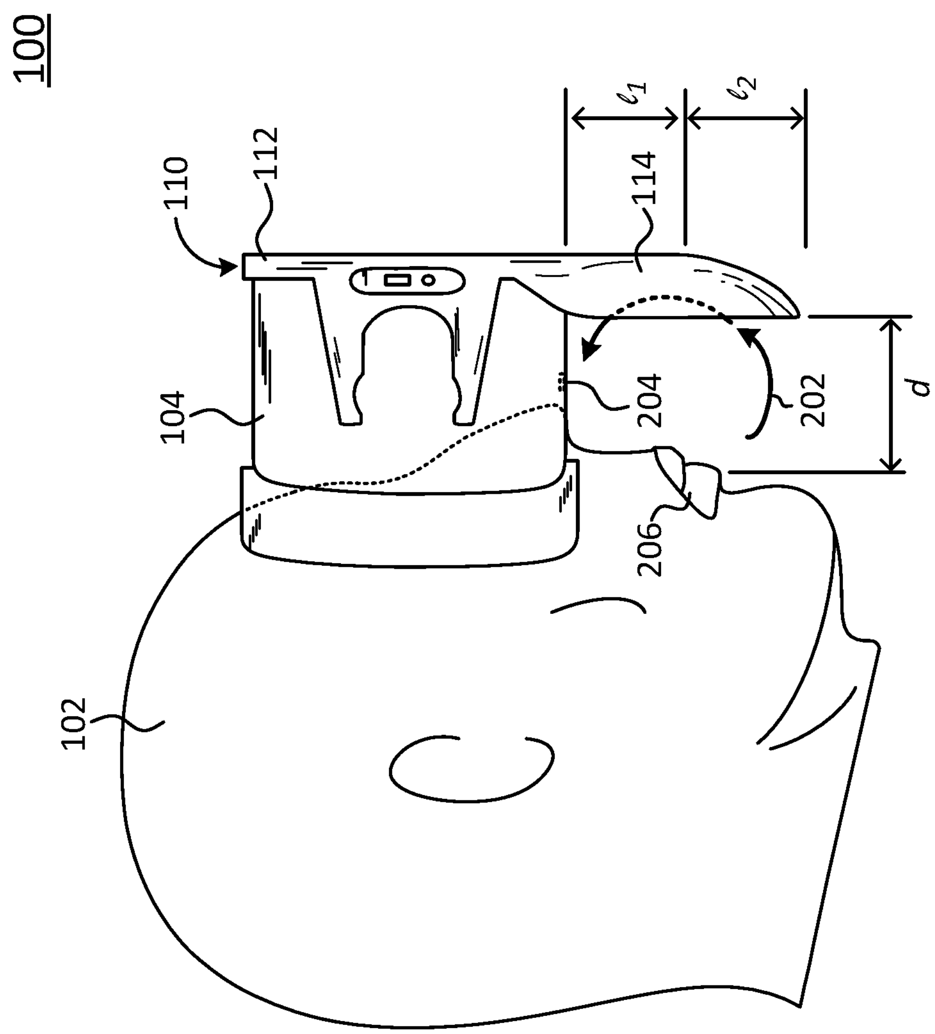
FIG. 2 illustrates a right side elevation view of the respiration guide device shown in FIG. 1, further showing the respiration guide device directing respired or exhaled air from a user toward an input component on the wearable headset.

FIG. 2 illustrates a right side elevation view of respiration monitoring system 100. In particular, FIG. 2 shows operations by curved baffle 114 to direct air and/or sound (e.g., vibrations) corresponding to respired air 202 (e.g., exhaled/inhaled air) from user 102 toward an input component 204 on wearable headset 104. Here, respired air 202 is illustrated as exhaled air, however it is also appreciated that the air can include inhaled air.

Input component 204 represents interfaces that operably measure metrics corresponding to the respired air (e.g., velocity, vibration, acceleration, temperature, amplitude, frequency, and so on). In some embodiments, input component 204 includes electronic interfaces that detect vibrations corresponding to the sound of respired air. For example, input component 204 can include voice coils, diaphragms, drivers, and other components such as those found in microphones and speakers. It is further appreciated that input component 204 is not be limited to a digital or electronic interface, but it may also include analog interfaces as well.

As shown, input component 204 is internally disposed within an interior of headset 104, however it is appreciated that input component 204 may be positioned in a plurality of other locations about or within headset 104 and/or external to headset 104 (e.g., in or on respiration guide device 110).

Input component 204 receives the air directed by curved baffle 114 and transforms the air into corresponding electrical signals, as is appreciated by those skilled in the art. As one example, input component 204 can include a diaphragm that vibrates or resonates at a frequency corresponding to the received air. The diaphragm's movement can move a voice coil through a magnetic field, which creates an electrical current (e.g., electrical signals). As is appreciated by those skilled in the art, the electrical signals are further processed by a processor to measure and generate biofeedback metrics corresponding to the respired air, and thus, the respiration of user 102.

Notably, the biofeedback metrics can include, for example, amplitudes, rates, volumes, etc. In some embodiments, the biofeedback metrics can be used by applications executing on headset 104 to improve user experiences and increase user engagement. For example, the biofeedback metrics may be used to adjust content presented to the user. Here, graphical elements may be generated and presented to the user. These graphical elements can include representations of the respiration metrics, including for example, numbers corresponding to a respiration rate, visualizations corresponding to virtually respired air (e.g., similar to condensation from an exhale on a cold day), and so on. In addition, the biofeedback metrics may adjust the content itself—e.g., increase or decrease the volume or speed of audio content, change color palettes to reflect faster or slower respiration rates, etc.

Still referring to FIG. 2, frame 112 includes a wall surface that downwardly depends or extends from frame 112 to form curved baffle 114. Preferably, the wall surface and curved baffle 114 are integrally formed (as shown). However, it also appreciated that the curved baffle and wall surface components may be separately formed.

Figure 7:
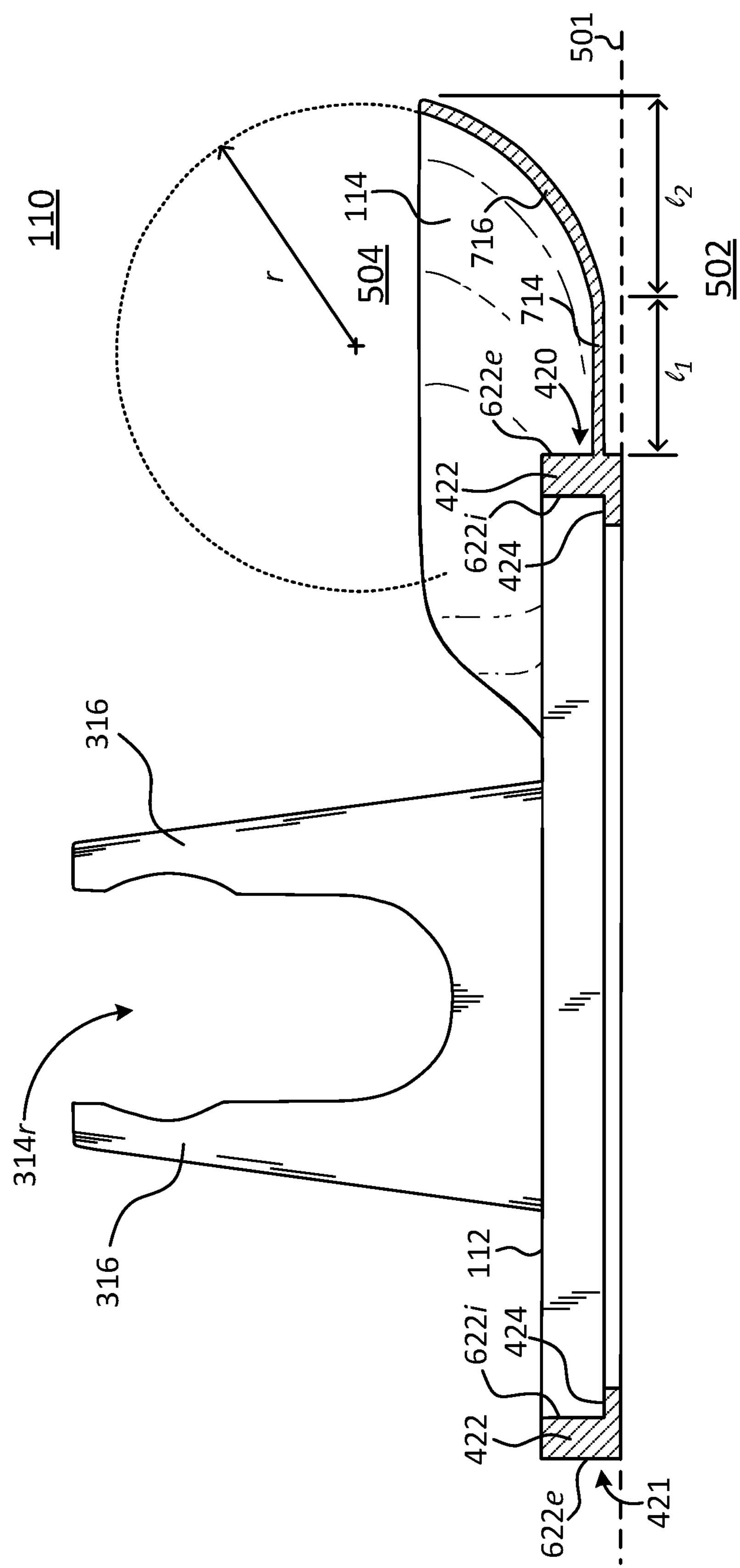
FIG. 7 illustrates a cross-sectional side elevation view of the respiration guide device shown in FIG. 6, viewed from cut lines 7-7.

Dimensions of curved baffle 114 are indicated by a length $l_1$ and a length $l_2$. Length $l_1$ and a length $l_2$ represent a total length of curved baffle 114 extending from a bottom portion of frame 112. In the side-elevation view shown in FIG. 2, length $l_1$ represents a length of a downwardly extending first portion of curved baffle 114 (e.g., the downwardly depending or descending wall surface) and length $l_2$ represents a second portion of curved baffle 114 having a curvature defined by one or more radaii (e.g., ref. FIG. 7 for further discussion). Notably, the curvature may be elliptical, spherical, or any other suitable curvature for directing respired air.

In operation, respiration guide device 110 is positioned relative to headset 104 such that curved baffle 114 is at a distance d relative to a mouth 206 of user 102 (e.g., a source of the respired air). Distance d represents to an optimal distance from mouth 206 to curved baffle 114 for facilitating operations by curved baffle 114 to direct respired air 202 (which can include sound vibrations). Distance d is determined as a function of a sensitivity of input component 204, a shape and size of the wall surface/curved baffle 114, a curvature of curved baffle 114, and a shape and size of headset 104. It is appreciated that different headsets can vary in size or shape, which may result in different distances d. Thus, distance d may be adjusted or varied in order to accommodate differently headsets.

As further shown in FIG. 2, respired air 202 from the user's mouth 206 traverses distance d toward curved baffle 114. Curved baffle 114 directs respired air 202 along its curved interior, along lengths $l_1$ and $l_2$ towards a bottom portion of frame 112 (not labeled, but shown in FIGS. 3 and 7). As discussed in greater detail below, frame 112 forms a seal, at least in part, about headset 104. This seal helps further direct the respired air 202 from the bottom portion of frame 112 toward input component 204 on headset 104.

Any combination and variation of distance d, length $l_1$, length $l_2$, and/or radius $r_1$ can be used to the direct the respired air (and/or sounds associated with the respired air) to/from the user's mouth 206 toward input component 204. In some embodiments, curved baffle 114 may adjustable such that it can be positioned at varying optimal distances d relative to the user's mouth 206.

Figure 3:
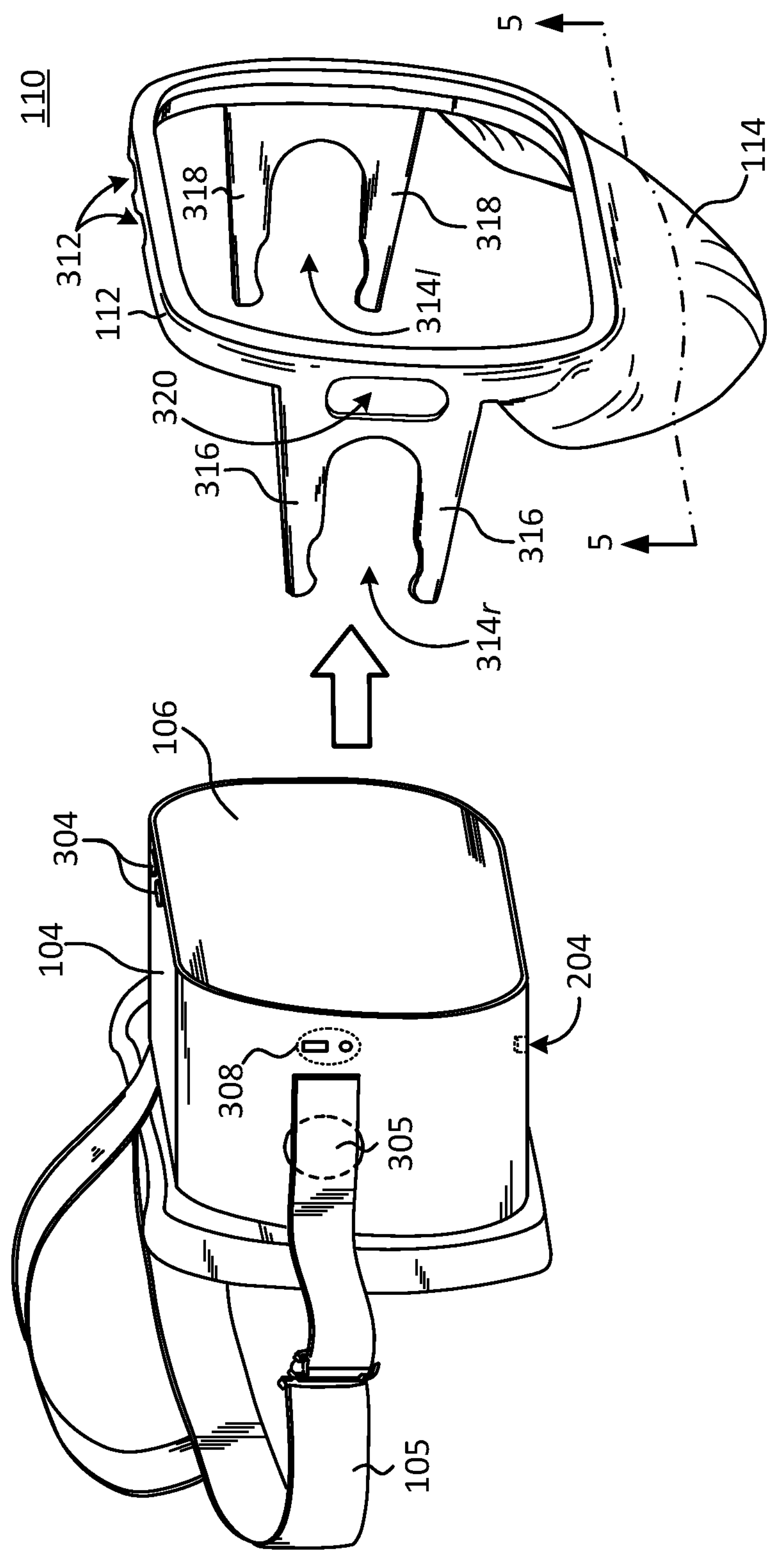
FIG. 3 illustrates an exploded front perspective view of the respiration monitoring system, shown in FIG. 1, showing the respiration guide device detached or decoupled from the wearable headset.

FIG. 3 illustrates an exploded front perspective view of respiration monitoring system 100, showing respiration guide device 110 detached or decoupled from headset 104.

As discussed, frame 112 of respiration guide device 110 couples or attaches to rear portion 106 of headset 104. In particular, frame 112 defines a frame perimeter dimensioned to surround (at least a portion of) a perimeter of headset 104 when attached to headset 104. In this fashion, the frame perimeter surrounds the perimeter of headset 104. As shown, the frame perimeter surrounds the whole perimeter of headset 104, however, in some embodiments, the frame perimeter need only surrounds a portion of the perimeter of headset 104.

FIG. 3 also shows one or more control buttons 304 positioned on a top side of headset 104 and one or more ports 308 positioned on a right side of headset 104. Control buttons 304 represent hardware components (e.g., switches, dials, buttons, etc.) for controlling various aspects of headset 104, including for example, power, volume, selection, and so on. Ports 308 represent interface components that allow a user to couple other electronic devices to headset 104. For example, ports 308 can include auxiliary ports, headphone ports, universal serial buses (USB), and so on. Again, it is appreciated that the illustrated control buttons and ports are representative of any type of input interface and/or control interface to headset 104. Other types of headsets may include additional or fewer buttons and/or ports as appreciated by those skilled in the art.

Frame 112 defines one or more grooves 312 and an aperture 320 to permit access to control buttons 304 and ports 308, respectively. In particular, aperture 320 defines an open space that permits access there-through to ports 308 (e.g., in the coupled or attached state). Similarly, grooves 312 permit access to control buttons 304 (e.g., when frame 112 is attached or coupled to headset 104).

Respiration guide device 110 also includes one or more attachment flanges such as flanges 316 and flanges 318. Here, flanges 316 and flanges 318 are disposed on frame 112 to form attachment mechanisms that releasably secure respiration guide 110 to headset 104. In particular, flanges 316 and flanges 318 define respective U-shaped cut-outs 314*r* (right) and 314/(left). These U-shaped cut-outs operably receive corresponding portions of headset 104 while flanges 316 and flanges 318 releasably couple to the corresponding portions of headset 104. For example, harness 105 is attached to headset 104 by a fastener or harness mount 305. When respiration guide 110 is attached to headset 104, cut-outs 314*r* and 3141 receive respective harness mounts 305. Flanges 316 and 318 clip or attach to respective harness mount(s) 305 to releasably secure frame 112 to headset 104.

Cut-outs 314*r* and 3141 are shown in a particular size and configuration for a specific headset (e.g., headset 104); however it is appreciated that the shape of the cut-outs and the corresponding flanges may be readily modified to fit other types of headsets. Moreover, while the attachment mechanisms formed by flanges 316 and 318 includes two pairs of flanges on either side of frame 112, it is also appreciated a single pair of flanges may be employed. Further, it is also appreciated a variety of other attachment mechanisms may also be employed and/or substituted for the pairs of flanges (e.g., friction fit attachments, adhesives, clasps, threaded attachments, a single attachment flange, multiple pairs of attachment flanges, etc.). Alternatively, in other embodiments, flanges 316 and 318 are optional. For example, in these alternative embodiments, the frame perimeter forms a friction fit seal about the perimeter of headset 104 to releasably secure frame 112 to headset 104.

Figure 4B:
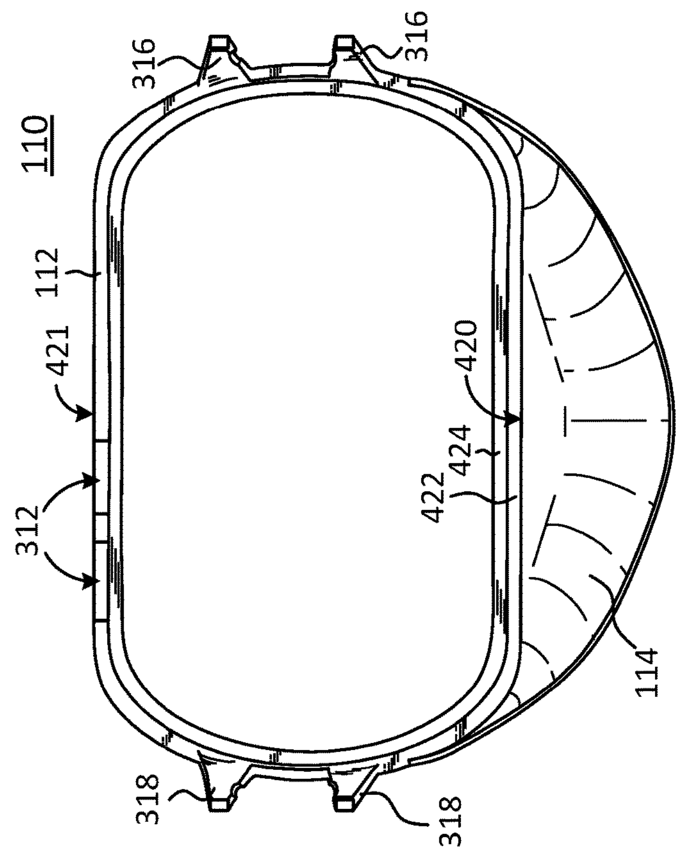
FIG. 4B illustrates a rear side elevation view of the respiration guide device shown in FIG. 1.
Figure 4A:
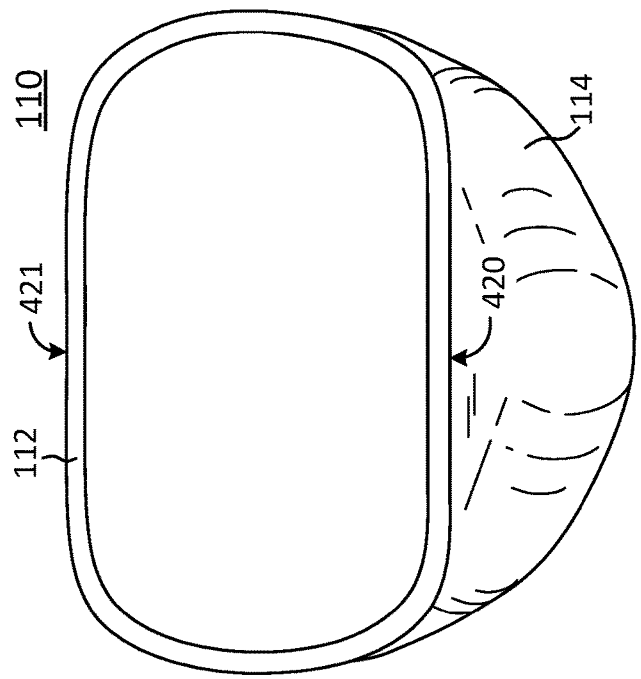
FIG. 4A illustrates a front side elevation view of the respiration guide device shown in FIG. 1.

FIG. 4A illustrates a front side elevation view of respiration guide device 110, and FIG. 4B illustrates a rear side elevation view of the same. In FIGS. 4A and 4B, frame 112 generally defines an oval or rounded rectangular shape, however it is appreciated that the shape of frame 112 may be modified based on the shape of the corresponding headset.

FIGS. 4A and 4B illustrate a bottom portion 420 of frame 112 and a top portion 421 of frame 112, opposite bottom portion 420. Bottom portion 420 generally refers a bottom or lower side of frame 112 that is positioned proximate to a bottom side of headset 104 when frame 112 is coupled to headset 104. Conversely, top portion 421 refers to a top or upper side of frame 112 that is positioned proximate to a top side of headset 104 when frame 112 is coupled to the same.

As discussed, a wall surface downwardly depends from a bottom portion of the frame 112—here, bottom portion 420—to form curved baffle 114. Curved baffle 114 has a generally parabolic curvature for collecting and directing respired air toward a focus—e.g., input component 204 of headset 104. As is appreciated by those skilled in the art, the parabolic curvature of curved baffle 114 may be modified based on the relative position of input component 204 (e.g., when respiration guide device 110 is coupled to headset 104). In addition, it is appreciated that curved baffle 114 can have elliptical, spherical, and/or asymmetrical curvatures. In general, the size, shape, and curvature of curved baffle 114 optimally directs the respired air toward input interface 204 of headset 104 (not shown here). Accordingly, the curvature is based on the location of input component 204 on headset 104 and the source of respired air (e.g., a user's mouth). At the same time however, it is also appreciated that relative improvements in directing the respired air from various types of curvatures may be balanced against aesthetics (e.g., look, appeal, consumer preferences, etc.).

Referring to FIG. 4B, the reference numbers corresponding to top portion 421 and bottom portion 420 generally refer to an exterior edge of a sidewall 422, where top portion 421 refers to a top or upper exterior edge portion of sidewall 422 and bottom portion 420 refers to a bottom or lower exterior edge portion of sidewall 422. Notably, sidewall 422 also defines an interior edge, opposite its exterior edge (e.g., ref. FIG. 7 and related discussion herein), which couples to headset 104.

Sidewall 422 defines a frame perimeter that substantially surrounds a corresponding perimeter of a housing of headset 104 (or a portion thereof). As shown in FIGS. 1 and 2, the frame perimeter defined by sidewall 422 surrounds the perimeter of rear portion 106 of headset 104 when respiration guide device 110 is attached or coupled to headset 104.

FIG. 4B also illustrates a skirt 424 disposed in frame 112 and between top portion 421 and bottom portion 420. As shown, skirt 424 is an interiorly recessed skirt that substantially surrounds an interior circumference of frame 112 (e.g., which interior circumference is defined by sidewall 422). Skirt 424 further forms a shoulder with sidewall 422, which receives a portion of headset 104 (e.g., rear portion 106) when respiration guide 110 is attached or coupled to headset 104. Here, the shoulder refers to the interior edge of sidewall 422. In operation, the shoulder interfaces with the rear portion of headset 104. In some embodiments, this shoulder forms an attachment mechanism coupled to the frame and provides a friction fit to releasably secure frame 112 to headset 104. In such embodiments, it is appreciated that the friction fit can provide sufficient force to secure frame 112 to headset 104 without requiring additional attachment mechanisms formed by flanges 316 and 318.

FIG. 4B further shows flanges 316 and 318 as integrally formed with frame 112, and more specifically, with sidewall 422. Flanges 316 and 318 operably protrude inward from an interior portion of frame 112 and form attachment mechanisms that releasably secure frame 112 to headset 104. In some embodiments, flanges 316 and 318 may be separately formed and joined or attached to frame 112.

Figure 5A:
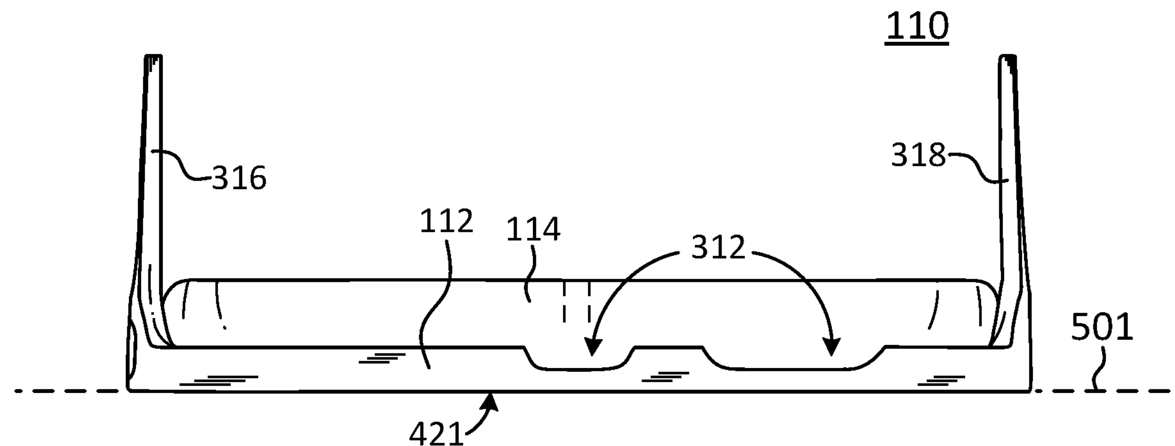
FIG. 5A illustrates a top side plan view of the respiration guide device shown in FIG. 1.
Figure 5B:
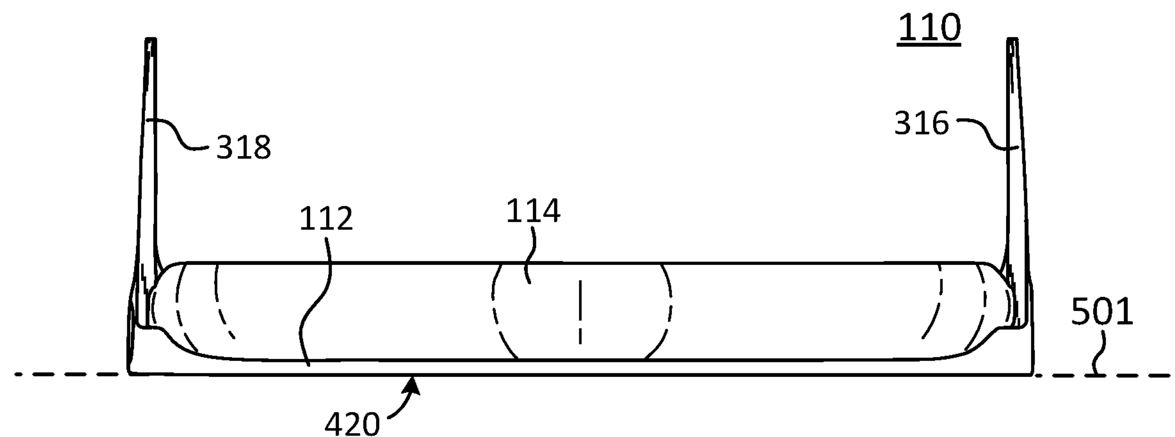
FIG. 5B illustrates a bottom side plan view of the respiration guide device shown in FIG. 1.
Figure 5C:
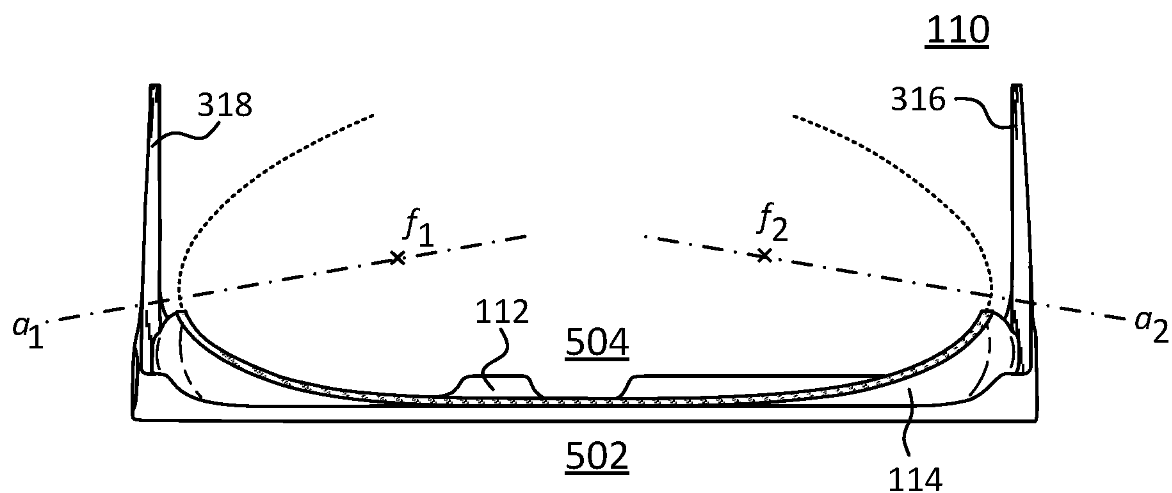
FIG. 5C illustrates a cross-sectional side plan view of the respiration guide device shown in FIG. 3, viewed from cut lines 5-5.

FIG. 5A illustrates a top side plan view of respiration guide device 110, FIG. 5B illustrates a bottom side plan view of respiration guide device 110, and FIG. 5C illustrates a cross-section side plan view of respiration guide device 110, viewed from cut lines 5-5 in FIG. 3.

FIG. 5A particularly illustrates grooves 312 defined along a top portion of frame 112. As discussed above, grooves 312 permit access to control buttons (e.g., control buttons 304) when respiration guide device 110 is attached to headset 104. It is appreciated that grooves 312 may modified to appropriate shapes and sizes depending on the type of headset and placement of control buttons (if any). FIG. 5B illustrates bottom portion 420 of frame 112, showing the lower exterior edge portion of sidewall 422.

FIGS. 5A and 5B also illustrate a frame plane 501 defined by an exterior perimeter of frame 112. As shown, frame plane 501 is represented as a dash line in the cross-sectional views of FIGS. 5A and 5B. Notably, flanges 316 and 318 extend or protrude from frame 112 at an angle substantially orthogonal to frame plane 501.

FIG. 5C illustrates a cross-sectional side plan view of respiration guide device 110 viewed along cut-lines 5-5 of FIG. 3. As discussed, curved baffle 114 may be constructed of a variety of different shapes and/or sizes to focus, guide, and/or otherwise direct the respired air from user 102 toward a desired focal point such as a bottom portion of frame 112, which corresponds to input component 204 when attached to headset 104.

Here, the cross-sectional view in FIG. 5C is a horizontal or lateral cross-sectional view of respiration guide device 110 that illustrates parabolic curvatures of curved baffle 114. For reference and discussion of the curvature of curved baffle 114, FIG. 5C illustrates reference numbers 502 and 504. Reference number 502 refers to an exterior side of respiration guide device 110 and reference number 504 refers to an interior side of respiration guide device 110, opposite the exterior side. "Interior side" and "exterior side" are relative terms, where the interior side refers to the inside of respiration guide device 110 (e.g., proximate to a user's face) when frame 112 is attached to headset 104, and the exterior side refers to the outside of respiration guide device 110 (e.g., distal or facing away from the user's face) when frame 112 is attached to headset 104.

As shown, the curvature of curved baffle 114 is represented by two parabolas, having respective foci, f1, f2, and respective axes of symmetry, a1 and a2. Here, curved baffle 114 is symmetrical about a centerline of frame 112 (not shown), such that the shape of curved baffle 114 on one side of the centerline is a mirror image of the shape of curved baffle on the other side of the centerline. Further, the curvature on either side of the centerline of frame 112 includes additional respective symmetries. For example, the parabola indicated by focus f1 is symmetrical about axis of symmetry a1, and the parabola indicated by focus f2 is symmetrical about axis of symmetry a2. With respect to interior side 504 and exterior side 502, curved baffle 114 curves away from exterior side 502 toward interior side 504 at the lateral cross-section shown in FIG. 5C.

In some embodiments, the respective axis of symmetry may be offset relative to each other to form an overall non-symmetrical curvature of curved baffle 114 (e.g., non-symmetrical as compared to the centerline of frame 112). Further, it is appreciated that the curvature indicated by two parabolas in this cross-sectional view is not limited to parabolic shapes, but may include any suitable shape (e.g., elliptical, circular, non-geometric shapes, etc.) for directing the respired air toward a portion of frame 112 and/or a portion of headset 104 (e.g., when attached to the headset).

In addition, curved baffle 114 includes a substantially smooth shape, however it is appreciated that curved baffle 114 may include interior ridges, ribs, and/or compartments that create partitions for segregating portions of air and/or sound corresponding to respired air. These partitions can provide additional structural integrity for curved baffle 114 and/or direct, amplify, or attenuate the air and/or sound corresponding to respired air as appropriate.

Further, while FIG. 5C illustrates the wall forming curved baffle 114 having specific cross-sectional area and shape, it is appreciated that curved baffle may have a thinner, thicker, and/or non-uniform cross sectional areas that provide proper structure and shape for directing the air toward a particular focus or position. Moreover, baffle 114 may be constructed of any suitable material to achieve the above, such as, but not limited to, acrylonitrile butadiene styrene (ABS) plastic, polyurethane, thermoplastic polymers, other plastics, rubber, wood, metals, etc. Further, although FIG. 5C illustrates baffle 114 as solid, baffle 114 may also be constructed to be porous, hollow, or of any other suitable density.

Figure 6:
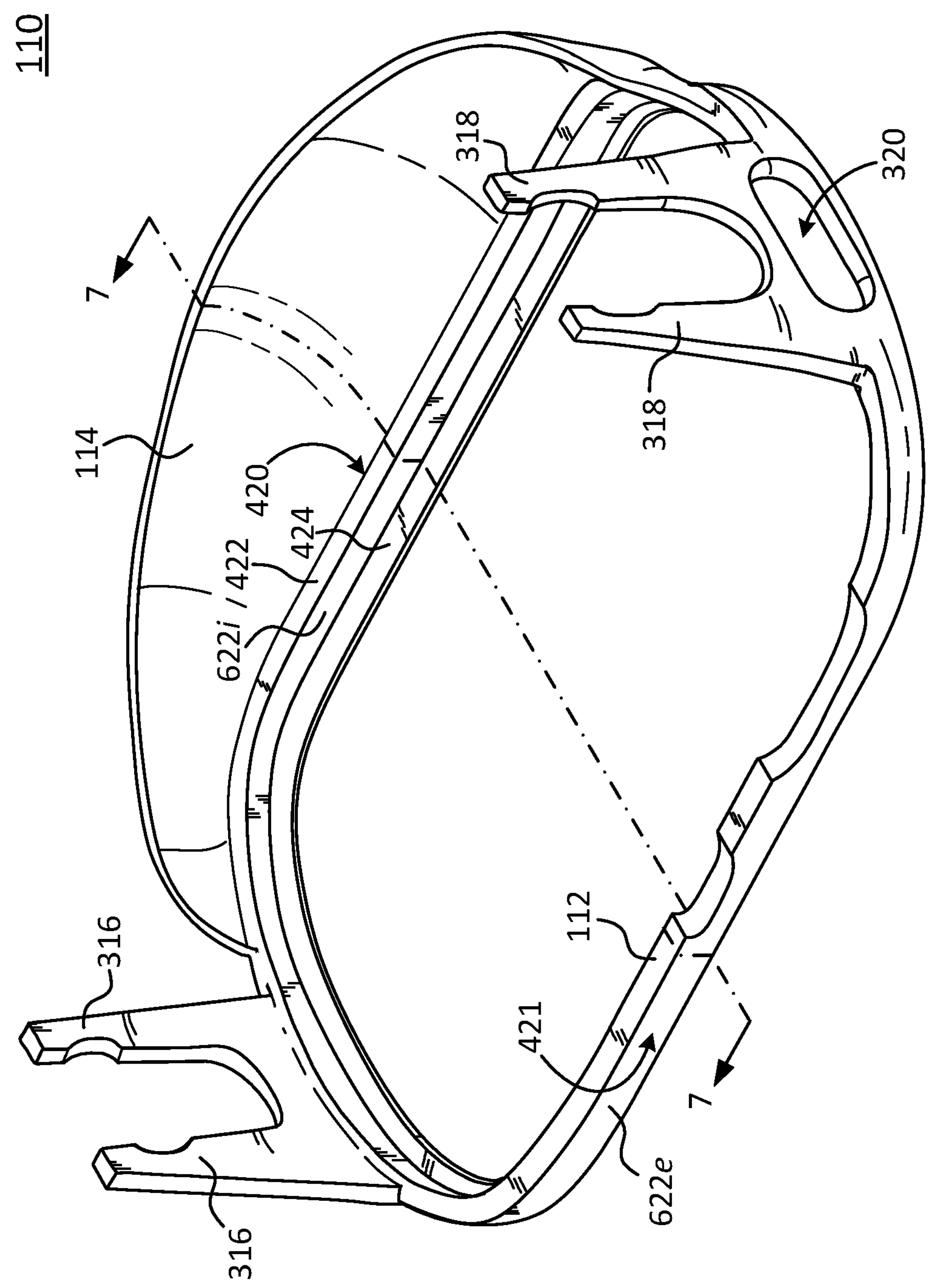
FIG. 6 illustrates a rear perspective view of a respiration guide device shown in FIG. 1.

FIG. 6 illustrates a rear perspective view of respiration guide device 110, showing an interior of respiration guide device 110 for receiving a portion of headset 104. As discussed above (ref. FIG. 4B), top portion 421 and bottom portion 420 generally refer to opposing portions of an exterior edge 622*e* of sidewall 422. As shown here, sidewall 422 includes exterior edge 622*e* and an interior edge 622*i*.

Further, FIG. 6 also illustrates skirt 424 disposed in frame 112. Skirt 424 is a recessed skirt that forms a shoulder with sidewall 422. The shoulder particularly abuts interior edge 622*i* of sidewall 422. In operation, frame 112 is releasably coupled to a headset—e.g., headset 104—such that a portion of the housing of the headset rests in interior recessed skirt 424 and on the shoulder (e.g., interior edge 622*i*). As discussed, frame 112 may be specifically sized such that recessed skirt 424 and interior edge 622*i* form a friction fit attachment mechanism to releasably couple frame 112 to the headset without requiring additional flanges (e.g., flanges 316/318). Here, the shoulder formed between interior edge 622*i* and skirt 424 is a circumferential shoulder about the interior perimeter of frame 112.

FIG. 7 illustrates a cross-sectional side elevation view of respiration guide device 110 shown in FIG. 6, viewed from cut lines 7-7. As shown, frame 112 includes a number of integrally formed components, including skirt 424, sidewall 422, and curved baffle 114. It is appreciated that the illustrated components may be separately formed and further, may be made of different materials with varying densities.

As shown, skirt 424 abuts sidewall 422 along its interior edge 622*i* to form a shoulder for receiving a portion of the headset. Similarly, curved baffle 114, which includes wall surface or a wall portion 714, abuts sidewall 422 along its exterior edge 622*e* and forms another shoulder opposite the shoulder formed by skirt 424 and interior edge 622*i*.

Importantly, the shoulder formed between skirt 424 and interior edge 622*i* operably forms a seal between frame 112 and a headset, which creates a partially confined space between curved baffle 114 and exterior edge 622*e*. In this fashion, skirt 424 and the shoulder formed with interior edge 622*i* define a socket that receives a rear portion of the headset (e.g., rear portion 106 of headset 104). Interior edge 622*i* defines the shape of the socket and skirt 424 defines a "bottom" of the socket. That is, the position and depth of the shoulder formed by skirt 424 and interior edge 622*i* determine the position of frame 112 relative to the headset (when attached). Typically, the depth of the shoulder is relatively shallow such that frame 112 is positioned proximate to a rear portion of the headset.

In some embodiments, however, frame 112 does not include a skirt 424. In these embodiments, interior edge 622*i* (only) forms couples to the housing of the headset and forms the seal between frame 112 and the headset. In these embodiments, frame 112 may be positioned along various portions of the housing of the headset (e.g., since there is no "bottom" of the socket). Further, in some embodiments, curved baffle 114 may not form a shoulder with exterior edge 622*e*. In these embodiments, curved baffle 114 may be formed with the same thickness as sidewall 422 and/or formed with a smooth tapering thickness from sidewall 422, which transitions in curved baffle 114.

With respect to the confined space between curved baffle 114 and exterior edge 622*e*, the shape is defined by the curvature of curved baffle 114. As discussed, this shape is selected to efficiently direct air toward a specific portion of frame 112 (e.g., bottom portion 420), and thus, toward a specific portion of the headset when frame 112 is attached to the same. As discussed, the headset shown through the figures of this application includes an input component (e.g., input component 204) that is located proximate to bottom portion 420 of frame 112 when frame 112 is attached to the headset. In this fashion, curved baffle 114 directs air corresponding to respired air toward bottom portion 420, and the input component of the headset further detects and measures the air to determine breathing metrics of the user (e.g., respiration rates, etc.).

FIG. 7 further illustrates wall surface or wall portion 714 downwardly depending from bottom portion 420 of frame 112 to form a curved portion 716 of curved baffle 114. In particular, wall portion 714 extends from bottom portion 420 by a first length $l_1$, while curved portion 716 extends from wall portion 714 by a second length $l_2$. Collectively, wall portion 714 and curved portion 716 form curved baffle 114. Notably, in some embodiments, curved baffle 114 may include multiple curvatures where, for example, wall portion 714 has a curvature different than that of curved portion 716.

The cross-sectional view shown in FIG. 7 is generally orthogonal to the cross-sectional view shown in FIG. 5. For example, the cross-sectional view of FIG. 5 is a horizontal or lateral cross-sectional view, viewed at cut lines 3-3 in FIG. 3, while the cross-sectional view of FIG. 7 is a vertical or longitudinal cross-sectional view, viewed at cut lines 7-7 in FIG. 6. Collectively, these cross-sectional views show various curvatures of curved baffle 114. For example, FIG. 5C illustrates curved baffle 114 curving away from exterior side 502 toward interior side 504 at a lateral cross-section (e.g., based on a parabolic curvature). FIG. 7 illustrates curved baffle 114 curving away from exterior side 502 toward interior side 504 at a longitudinal cross-section (e.g., based on an elliptical or spherical curvature). In this fashion, curved baffle 114 curves away from exterior side 502 toward interior side 504 based on a first or lateral cross-section and a second or longitudinal cross-section orthogonal to the first cross section.

As shown, curved baffle 114 has a circular or elliptical cross-sectional shape indicated by radius r. It is also appreciated that curved baffle 114 can include any number of shapes and curvatures (e.g., parabolic, etc.) and further, the shape and curvature need not be symmetrical about any center line or center plane of frame 112. In general, the curvature of curved baffle 114 is shaped and dimensioned for optimizing directing air corresponding to respiration toward a particular position, which position typically corresponds to the position of an input component of the headset when attached to frame 112.

Figure 8A:
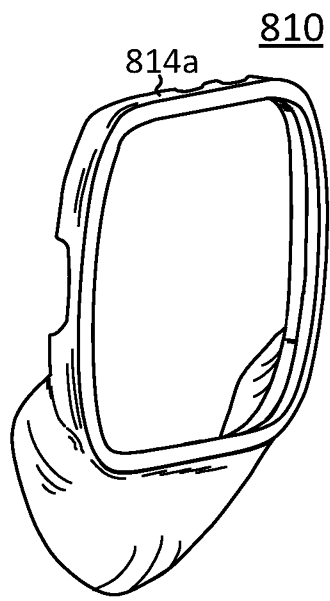
FIGS. 8A, 8B, and 8C illustrate respective perspective views of additional embodiment of respiration guide devices, according to one or more examples of this disclosure.
Figure 8B:
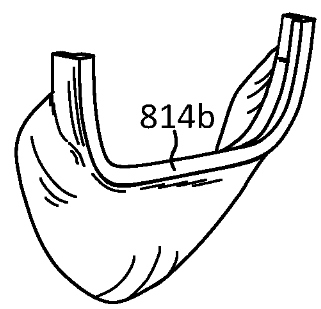
Figure 8C:
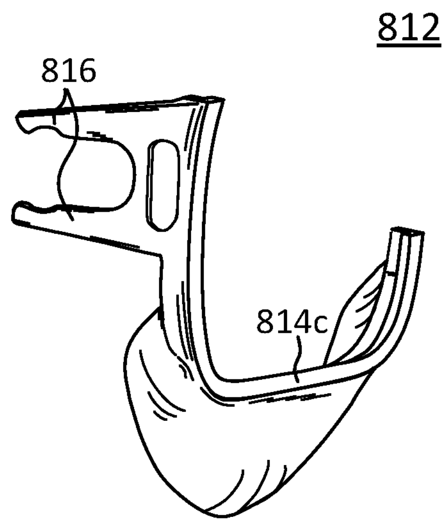

FIGS. 8A, 8B, and 8C illustrate respective perspective views of additional embodiments of respiration guide devices. In particular, FIG. 8A illustrates a respiration guide device 810 having a frame 814*a* that forms a friction fit with a corresponding headset. Here, frame 814*a* defines a circumferential perimeter that forms a friction fit attachment mechanism, where the circumferential perimeter couples to a corresponding perimeter of the housing of the headset.

FIG. 8B illustrates a respiration guide device 811 having a partially circumferential frame 814*b*. In this embodiment, respiration guide device 811 may couple to a corresponding headset by, for example, fasteners (not shown), adhesives, and so on.

FIG. 8C illustrates a respiration guide device 812 having a partial circumferential frame 814*c* and one set of flanges 816, where flanges 816 form an attachment mechanism that couples frame 814*c* to the headset.

Figure 9:
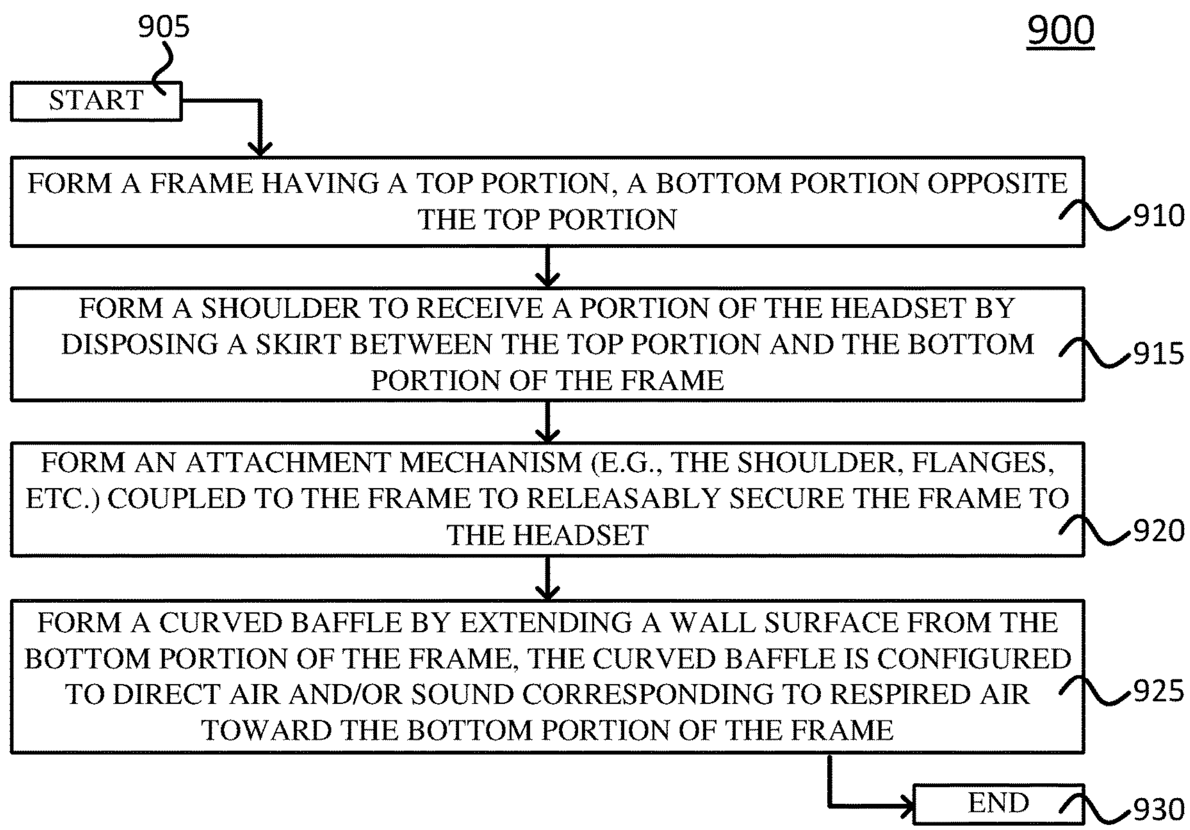
FIG. 9 illustrates a schematic block diagram of a procedure for forming a respiration guide device, according to one or more examples of this disclosure.

FIG. 9 illustrates a schematic block diagram of a procedure 900 for forming a respiration guide device according to one or more examples of this disclosure. Process 900 begins with step 905, and continues to step 910 where a frame is formed. Notably, the frame has a top portion (e.g., top portion 421) and a bottom portion (e.g., bottom portion 420) opposite the top portion.

Procedure 900 continues to step 915 where a shoulder is formed to receive a portion of the headset. For example, the shoulder can be formed by disposing a skirt between the top portion and the bottom portion of the frame. As discussed above, this shoulder can be formed as an interior recessed skirt (e.g., skirt 424) and disposed along an interior edge (e.g., interior edge 622*i*) of a sidewall (e.g., sidewall 422) of the frame (e.g., frame 112).

At step 920, an attachment mechanism is formed and coupled to the frame to releasably secure the frame to the headset. As mentioned, in some embodiments, the attachment mechanisms can include a friction fit attachment mechanism formed by the recessed skirt, the shoulder, the sidewall, and/or one or more flanges. With respect to the flanges, the flanges (e.g., flanges 316, 318) can protrude or extend at an angle substantially orthogonal to a frame plane (e.g., frame plane 501).

A curved baffle is formed at step 925. The curved baffle is particularly formed by extending a wall surface from a bottom portion of the frame (e.g., from a bottom portion of sidewall 422 of frame 112). Notably, the curved baffle is operable or configured to direct air and/or sound corresponding to respired air toward the bottom portion of the frame. In operation, when the frame is attached to a headset, the bottom portion of the frame further corresponds to an input interface on the headset. Thus, when attached to a headset, the curved baffle directs the air and/or sound toward the input interface on the headset. Process 900 subsequently ends at step 930.

Procedure 900 illustrates exemplary operations for forming a respiration guide device. These operations can represent a molding process. Further, as noted above, each of these steps can be performed during a single molding process or as part of a multi-step molding process. It should also be noted that certain steps within procedure 900 may be optional, and further, the steps shown in FIG. 9 are merely example steps for illustration. Further, while a particular order of the steps is shown, this ordering is merely illustrative, and any suitable arrangement of the steps may be utilized without departing from the scope of the embodiments herein.

While there have been shown and described illustrative examples of the respiration guide device, it is to be understood that various other adaptations and modifications may be made within the spirit and scope of the embodiments herein. For example, the embodiments and operations disclosed herein have been described with respect to a curved baffle; however it is appreciated that such embodiments are provided for purposes of example and illustration, not limitation. In some embodiments, the curved baffle need not be "curved" according to a traditional radius or geometric shape, but instead, the curved baffle can include a number of flat surfaces coupled at relative angles to form an overall "curvature" for directing air and/or sound corresponding to respired air toward a given position. Further while the respiration guide devices shown and described herein are standalone accessories that can be coupled to various headsets, it is appreciated that such respiration guide devices may be incorporated into future designs of headset designs and need not be separate/standalone devices. Moreover, the input interfaces are shown and described as part of the headset; however it is also appreciated that such input interfaces can be readily incorporated into the disclosed respiration guide devices. For example, the respiration guide devices can include appropriate electronics (hardware/software) for detecting and measuring metrics corresponding to respired air, and further communicate such data corresponding to the sound to the headset (e.g., by wired or wireless communications). Thus, while the foregoing description has been directed to specific embodiments, it will be apparent that other variations and modifications may be made to the described embodiments, with the attainment of some or all of their advantages. Accordingly this description is to be taken only by way of example and not to otherwise limit the scope of the embodiments herein. Therefore, it is the object of the appended claims to cover all such variations and modifications as come within the true spirit and scope of the embodiments herein.

The invention claimed is:

1. A device for directing respired air, the device comprising:

a frame having a top portion, a bottom portion opposite the top portion, and at least one shoulder disposed between the top portion and the bottom portion to receive a portion of a headset, and a wall surface; and an attachment mechanism coupled to the frame, the attachment mechanism is operable to releasably secure the frame to the headset, wherein the wall surface of the frame downwardly extends from the bottom portion of the frame to form a curved baffle, the curved baffle is operable to direct air corresponding to respiration toward the bottom portion of the frame.

2. The device of claim 1, wherein the frame defines a frame plane, and wherein the attachment mechanism includes at least one flange that protrudes from the frame at an angle substantially orthogonal to the frame plane.

3. The device of claim 1, wherein the wall surface includes a first portion downwardly depending from the frame and a second portion connected to the first portion, wherein the second portion defines a curvature of the curved baffle.

4. The device of claim 1, further comprising:

a skirt disposed in the frame, the skirt forming the at least one shoulder with an interior sidewall of the frame.

5. The device of claim 4, wherein the skirt and the at least one shoulder form the attachment mechanism.

6. The device of claim 1, wherein the headset includes a headset housing, wherein the frame is operable to surround at least a portion of the headset housing.

7. The device of claim 1, wherein the curved baffle has at least one of a parabolic curvature, a circular curvature, or an elliptical curvature.

8. The device of claim 1, wherein the frame has an exterior side and an interior side opposite the exterior side, wherein the curved baffle curves away from the exterior side toward the interior side at a lateral cross-section of the frame, and wherein the curved baffle curves away from the exterior side toward the interior side at a longitudinal cross-section orthogonal to the lateral cross-section.

9. The device of claim 8, wherein the curved baffle has a first curvature at the lateral cross-section of the device and a second curvature, different than the first curvature at the longitudinal cross-section of the device.

10. The device of claim 1, wherein the frame defines at least one aperture that provides access to one or more control interfaces of the headset.

11. The device of claim 1, wherein the frame defines at least one notch in the top portion to provide access to one or more control interfaces on the headset.

12. A system, comprising:

a frame having a baffle and an interior recessed skirt that forms a shoulder operable to receive a portion of a headset; and an attachment mechanism coupled to the frame, the attachment mechanism is operable to releasably secure the frame to the headset, wherein the baffle downwardly extends from a bottom portion of the frame, the baffle is operable to direct air corresponding to respiration toward a bottom portion of the frame.

13. The system of claim 12, wherein the baffle has at least one curvature for directing the air toward the bottom portion of the frame.

14. The system of claim 12, wherein the frame defines a frame plane, and wherein the attachment mechanism includes at least one flange that protrudes from the frame at an angle substantially orthogonal to the frame plane.

15. The system of claim 12, wherein the attachment mechanism is integrally formed with the frame.

16. The system of claim 12, wherein the frame has an exterior side and an interior side opposite the exterior side, wherein the baffle curves away from the exterior side toward the interior side at a lateral cross-section of the frame, and wherein the curved baffle curves away from the exterior side toward the interior side at a longitudinal cross-section orthogonal to the lateral cross-section.

17. The system of claim 12, wherein the baffle has at least one of a parabolic curvature, a circular curvature, or an elliptical curvature.

18. The system of claim 12, wherein the headset includes a headset housing having a front portion for interfacing with a portion of a user's head and a rear portion opposite the front portion, wherein the frame is operable to surround at least a portion of the headset housing.

19. The system of claim 12, further comprising the headset, wherein the headset further includes at least one input interface, wherein the baffle has a curvature for directing the air toward the at least one input interface when the frame is releasably secured to the headset.

20. A method of forming a device that directs respired air, the method comprising:

forming a frame having a top portion, a bottom portion opposite the top portion, and a wall surface;

forming at least one shoulder disposed between the top portion and the bottom portion to receive a portion of a headset;

forming an attachment mechanism coupled to the frame, the attachment mechanism is operable to releasably secure the frame to the headset; and forming a curved baffle by extending the wall surface downward from the bottom portion of the frame, the curved baffle is operable to direct air corresponding to respiration toward the bottom portion of the frame.

* * * * *